United States Patent [19]

Devaux et al.

[11] Patent Number: 4,657,956
[45] Date of Patent: Apr. 14, 1987

[54] COMPOUNDS USEFUL AS STABILIZING AGENTS FOR RUBBER VULCANIZATES

[75] Inventors: Albert F. L. G. Devaux, Mont Saint Guibert; Philippe G. Moniotte, Heron, both of Belgium

[73] Assignee: Monsanto Europe, S. A., Brussels, Belgium

[21] Appl. No.: 775,555

[22] Filed: Sep. 13, 1985

Related U.S. Application Data

[62] Division of Ser. No. 617,070, Jun. 4, 1984, Pat. No. 4,595,721.

[51] Int. Cl.$^4$ .................. C08K 5/41; C08K 5/36; C07C 149/26; C07C 149/14; C07D 403/12
[52] U.S. Cl. .................. 524/105; 260/429.9; 524/106; 524/170; 524/208; 524/289; 524/223; 524/303; 524/357; 524/393; 548/376; 560/145; 560/152; 560/153; 560/154; 564/154; 568/31; 568/42; 568/43; 568/56; 568/477; 568/413
[58] Field of Search .................. 568/31, 56, 377, 413, 568/42, 43; 564/154; 548/376; 558/11; 524/393, 303, 208, 357, 223, 105, 106, 170, 289; 560/145, 152, 153, 154; 260/429.9

[56] References Cited

U.S. PATENT DOCUMENTS

| | | | |
|---|---|---|---|
| 2,135,987 | 11/1938 | Murphy | 558/11 |
| 2,169,700 | 8/1939 | Loane | 558/11 |
| 2,530,872 | 11/1950 | Gregory et al. | 560/154 |
| 2,677,617 | 5/1954 | Thompson | 568/29 |
| 2,855,339 | 10/1958 | Klopping | 558/11 |
| 3,212,963 | 10/1965 | Wehner | 564/154 |
| 3,479,408 | 11/1969 | Perrino et al. | 568/29 |
| 4,256,659 | 3/1981 | Wheeler | 564/154 |
| 4,271,050 | 6/1981 | Maender | 568/43 |

OTHER PUBLICATIONS

Yoshida: *Tetrahedron*, 26 (12) 2987–93 (1970).
Chemical Abstracts 33:5825-7, "Polymethylenebisthionylacetic Acid," Erik Larsson.
Chemical Abstracts 39:1586-4, "Complex Compounds Between Ag and Some S-Containing Carboxylic Acid Ions in Aqueous Solution," Erik Larsson.
"Studies on Antitumor Substances IX," Chemical Behaviors of Thiosulfonate Toward Active Methylene Compound, Seigoro Hayashi et al, Chemical & Pharmaceutical Bulletin, vol. 17, No. 3, Mar. 1969.

*Primary Examiner*—Veronica P. Hoke
*Attorney, Agent, or Firm*—Gordon B. Seward

[57] ABSTRACT

Additives for rubber compositions, giving vulcanizates having improved retention of optimum physical properties, are compounds having the formula R—S—B—S—R where B is an organic bridging group and R is an electron-withdrawing group, for example CN, CCl$_3$, a radical containing an activated methylene group linked to the sulphur atom or the enolic tautomer of a keto-activated methylene group. Also useful as stabilizing agents are oligomeric analogues of such compounds.

22 Claims, No Drawings

COMPOUNDS USEFUL AS STABILIZING AGENTS FOR RUBBER VULCANIZATES

This is a division of application Ser. No. 617,070, filed June 4, 1984, now U.S. Pat. No. 4,595,721, filed June 17, 1986.

This invention relates to rubber vulcanisates having improved physical properties.

The process of vulcanising diene rubbers by heating with sulphur and a vulcanisation accelerator has been known for many years. By this process vulcanisates having certain physical properties, for instance tensile strength, resilience and fatigue resistance at a high level can be obtained, but such vulcanisates tend not to have good ageing properties. Apart from the addition of antioxidants which will retard oxidative heat ageing, other methods which have been proposed for making vulcanisates having improved ageing properties include the use of lower proportions of sulphur and increased proportions of accelerator relative to those which would be employed for a conventional cure, and the partial or complete replacement of sulphur by other cross-linking agents. Examples of such cross-linking agents include amine disulphides, for example N,N'-dithiodimorpholine, bis(sulphenamides) as described in GB Patent Specification No. 1,409,953 and U.S. Pat. No. 3,847,880, and compounds comprising two or more accelerator groupings linked through an organic bridging group as described in GB Patent Specification 1,388,279.

Vulcanisates made using such alternative systems tend, however, to lack certain of the merits of a sulphur-cured vulcanisate. For example, lowering the ratio of sulphur to accelerator or replacing the sulphur partially or completely by an amine disulphide, gives vulcanisates having inferior dynamic properties. The use of the aforementioned bis(sulphenamides) and compounds containing two or more accelerator groupings means that molecular species having accelerator activity as well as those having cross-linking activity are released into the vulcanising system, so that the freedom for variations in compounding, which is possible when the cross-linking agent and the accelerator are added as separate entities, is lost.

According to the present invention we have found that vulcanisates having improved properties can be obtained by adding certain materials in addition to sulphur and a vulcanisation accelerator during the compounding of diene rubbers. These materials have the effect of stabilising the properties of the vulcanisate if the temperature of the vulcanisate unavoidably remains high for a prolonged period after cure, and during the service life of the vulcanisate, and are herein referred to as stabiliser materials.

The invention provides a vulcanisable rubber composition comprising a diene rubber, sulphur and a vulcanisation accelerator, characterised in that the composition also comprises a stabiliser material have the formula (a) R—S—B—S—R where B is an organic bridging group and R is (i) a group having the formula

where $R^1$ is H or $C_{1-6}$ alkyl, and $R^2$ and $R^3$ are each independently CN, $CONHR^4$, $COR^5$, $COOR^5$, $SO_2R^5$, COOM or $SO_2OM$, where $R^4$ is H, $C_{1-6}$ alkyl, phenyl or benzyl, $R^5$ is $C_{1-6}$ alkyl, phenyl or benzyl, and one of $R^2$ and $R^3$ can also be H, M represents H, a monovalent metal, the equivalent of a multivalent metal, an ion derived from a mono-acid nitrogenous base or the equivalent of an ion derived from a poly-acid nitrogenous base, (ii) a group having the formula

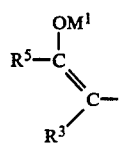

in which $M^1$ represents H, a monovalent metal or the equivalent of a multivalent metal, $R^3$ and $R^5$ being as defined above, except that $R^3$ cannot be H, or in which $R^3$ and $R^5$ are linked to form a cyclic group; or (iii) CN or $CCl_3$; or

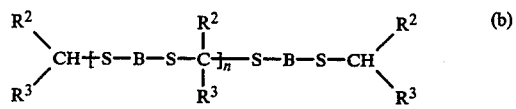

The invention also includes a vulcanisate that has been obtained by heating a vulcanisable rubber composition of the invention at a vulcanisation temperature.

Many of the materials useful as vulcanisate stabilisers in accordance with the invention are new, and a further aspect of the invention is a compound having formula (a) above in which B is an alkylene group having from 5 to 16 carbon atoms or a ($C_{1-6}$ alkylene)cycloalkylene or a ($C_{1-6}$ alkylene)alkylcycloalkylene group and R is a group having formula (i) where $R^1$ is H and $R^2$ and $R^3$ are each independently CN, $CONHR^4$, $COOR^5$, $SO_2R^5$ where $R^4$ is H, $C_{1-6}$ alkyl or benzyl, and $R^5$ is $C_{1-6}$ alkyl, phenyl or benzyl, a group having formula (i) where $R^1$ and $R^2$ are both H and $R^3$ is a group having the formula —$CH_2$—COOM, where M represents hydrogen, a monovalent metal, an equivalent of a multivalent metal or an ion derived from a monoacid nitrogenous base, provided that M is not hydrogen or an alkali metal when B is an alkylene group having from 5 to 16 carbon atoms, a group having formula (ii) in which $M^1$ represents H, a monovalent metal or the equivalent of a multivalent metal, $R^3$ represents $CONHR^4$ or $COR^5$ where $R^4$ is H, $C_{1-6}$ alkyl, phenyl or benzyl, and $R^5$ is $C_{1-6}$ alkyl, phenyl or benzyl, or in which $R^3$ and $R^5$ are linked such that each R is a group having the formula

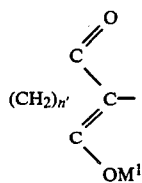

where n' has the value 2 or 3 and one or more of the hydrogen atoms in the $(CH_2)_{n'}$ grouping can be replaced by methyl or ethyl groups a group $CCl_3$;

or a material having formula (b) above in which B represents an alkylene group of from 5 to 16 carbon atoms, $R^2$ and $R^3$ are each independently CN, $CONHR^4$ or $COOR^5$ where $R^4$ is H, $C_{1-6}$ alkyl, phenyl or benzyl, $R^5$ is $C_{1-6}$ alkyl, phenyl or benzyl, and n has an average value of from 1 to 5.

In the above formulae of the stabiliser material, B can be, for example, a straight- or branched-chain alkylene or alkenylene group, preferably one containing 2 or from 5 to 40 carbon atoms, and more preferably one containing 5 to 16 carbon atoms. Examples of such groups are ethylene, pentamethylene, hexamethylene, octamethylene, nonamethylene, decamethylene, hexadecamethylene, 3-methyl-1,5-pentylene and 1,6-hex-2-enylene. As a variant, a divalent bridging group may be an alkylene or alkenylene group having one or more aryl, for example phenyl, substituents. An example of such a radical is 2-phenyl-1,4-pentylene.

Alternatively, B can be a cycloalkylene or alkylenecycloalkylene group. In such groups, the ring is usually cyclopentylene or cyclohexylene. The alkylene radical in alkylenecycloalkylene groups can have, for example, from 1 to 6 carbon atoms arranged in either a straight or branched chain. Also included are groups in which the ring is cycloalkylene or alkylenecycloalkylene groups carries up to three alkyl substituents, each of which typically has 1–4 carbon atoms, for example methyl, ethyl, or isopropyl. Examples of these cycloalkylene and alkylenecycloalkylene groups are 1,4-cyclohexylene; (2'-ethylene)cyclohexylene groups, e.g. 4(2'-ethylene)cyclohexylene; (2'-ethylene)methylcyclohexylene groups, e.g. 4(2'-ethylene)-3-methylcyclohexylene; (2'-isopropylene)cyclohexylene groups; and (2'-isopropylene)methylcyclohexylene groups, e.g. 2-methyl-5(2'-isopropylene)cyclohexylene.

In other instances, B has a structure comprising two or more alkylene units, pairs of such units being linked through an oxygen or sulphur atom, through a group —COO—, or through an arylene or cycloalkylene radical.

Representative of such structures are those of the formulae

—$(CH_2)_a$—O—$(CH_2)_a$—
—$(CH_2)_a$—O—$(CH_2)_{a'}$—O—$(CH_2)_a$—
—$(CH_2)_b$—A—$(CH_2)_b$—
—$(CH_2)_c$—COO—$(CH_2)_a$— and
—$(CH_2)_c$—COO—Y—OOC—$(CH_2)_c$—, where each a' and each c independently represents an integer of from 1 to 20, a represents an integer of from 2 to 20, each b independently represents an integer of from 1 to 10, A represents phenylene or cyclohexylene, and Y represents a group —$(CH_2)_c$— or a group —$(CH_2CH_2O)_d CH_2CH_2$— where d represents an integer of from 1 to 5. Preferred values for a are from 2 to 8, preferred values for b are 1 to 4, and preferred values for c are from 1 to 18, more especially 1 to 12.

Other examples of the bridging group B are those having the formula

—$(CH_2)_c$—$SO_2$—$(CH_2)_c$—
—$(CH_2)_c$—NH—$(CH_2)_c$— and
—$(CH_2)_c$—$NH_2{}^+$—$(CH_2)_c$— where each c independently has a value from 1 to 20, preferably from 3 to 18, and more preferably from 3 to 12.

Where values of a, b, or c exceed 2, the poly methylene groups can be straight chain or branched, but in most instances the terminal carbon atom to which the —S—R— or —S—X— group is attached is a primary carbon atom.

The optimum number of carbon atoms in the alkylene units to which the sulphur atoms are attached to a bridging group of the kind described above where two or more units are linked through atoms or groups, depends on the remainder of the structure of the bridging group.

A further requirement is that the relative locations of the sulphur atoms in the grouping —S—B—S should not be such that significant intramolecular cyclisation can occur when a rubber composition containing the stabiliser material is heated. For example, compounds in which the bridging group is trimethylene or tetramethylene show little stabiliser activity, and it is believed that this is due to the tendency of such compounds to cyclise.

Thus within the class of compounds defined above there will be found differing degrees of stabiliser activity, but methods of evaluation as subsequently described are conventional, and it is therefore a matter of simple and minimum experimentation for the person skilled in the art to determine whether a particular compound will usefully stabilise rubber compositions.

When M or $M^1$ is the above formula of the stabiliser material represents a monovalent metal, this can be for instance an alkali metal, for example sodium, lithium or potassium. Sodium is the preferred alkali metal. M or $M^1$ can alternatively represent the equivalent of a multivalent metal, for instance magnesium, calcium, barium, zinc, nickel, cobalt, aluminium or copper.

Where M represents a monovalent ion derived from a mono-acid nitrogenous base, the nitrogenous base can be ammonia or a simple primary, secondary or tertiary amine.

$R^6NH_2$, $R^6R^7NH$ or $R^6R^7R^8N$ where
each of $R^6$, $R^7$ and $R^8$ independently represents an alkyl group, for example a $C_{1-20}$ alkyl group, a $C_{5-9}$ cycloalkyl or alkylcycloalkyl group, for example cyclohexyl or methylcyclohexyl, a benzyl group, a phenyl group or a substituted phenyl group, for example a tolyl or chlorophenyl group, provided that not more than one of $R^6$, $R^7$ and $R^8$ is a phenyl or substituted phenyl group.

Preferred amines are those that are relatively weakly basic. These include amines where weak basicity is a result of steric hindrance around the nitrogen atom due, for example, to the presence of a tert-alkyl group, for instance a tert-alkyl group having from 4 to 12 carbon atoms, such as tert-butyl, tert-amyl or 1,1,3,3-tetramethylbutyl. Examples of such amines are the secondary amines $R^6R^7NH$ where one of $R^6$ and $R^7$ is a tert-alkyl group and the other is a benzyl group or a cyclohexyl or alkylcyclohexyl group. Alternatively both $R^6$ and $R^7$ can be tert-alkyl groups. Further examples are tertiary amines where $R^6$ is a tert alkyl group and $R^7$ and $R^8$ are benzyl groups.

Other suitable weakly basic amines are the primary amines $R^6NH_2$ where $R^6$ is a phenyl or substituted phenyl group, and the secondary amines $R^6R^7NH$ where $R^6$ is a phenyl or substituted phenyl group and $R^7$ is a $C_{1-20}$ alkyl group, preferably a $C_{1-12}$ group. Examples of such amines are aniline, the toluidines, N-methylaniline, N-butylaniline and N-isohexylaniline. A special class of such secondary amines comprises those where $R^6$ represents a secondary alkyl group, preferably a $C_{3-12}$ secondary alkyl group, or a cyclohexyl group, and $R^7$ represents a 4-phenyl-aminophenyl group. These amines include compounds such as N-iso-propyl-N'-phenyl-p-phenylenediamine, N-sec-butyl-N'-phenyl-p-phenylenediamine, N-1,3-dimethylbutyl-N'-phenyl p-phenylenediamine, N-1,4-dimethylpentyl-N'-phenyl-p-phenylenediamine and N-cyclohexyl-N'-phenyl-p-phenylenediamine. Such amines function as mono-acid bases despite the presence of the second nitrogen atom in the 4-phenylaminophenyl group, because this second nitrogen atom has virtually no basicity.

Where M represents an equivalent of the multivalent cation formed by the addition of two or more protons to a nitrogenous base, the bases from which such ions can be derived include alkylene diamines, N,N'-disubstituted alkylene diamines, phenylenediamines and N,N'-disubstituted phenylenediamines of the formula $$R^6\text{—NH—A—NHR}^6$$

where A represents an alkylene radical $-(CH_2)_c-$ where c has a value of from 2 to 20, preferably from 2 to 12, and which may be straight chain or branched, or a phenylene, for example a meta- or para-phenylene radical, and each $R^6$ independently represents an alkyl group, for example a $C_{1-20}$ alkyl group, a $C_{5-9}$ cycloalkyl or alkylcycloalkyl group, a benzyl group, a phenyl group or substituted phenyl group, provided that neither $R^6$ is a phenyl or substituted phenyl group when A is a phenylene radical.

In preferred amines where A represents an alkylene radical, $R^6$ is a tert-alkyl group, for example tert-butyl, t-amyl or 1,1,3,3-tetramethylbutyl, or a phenyl group. Examples of such amines are N,N'-diphenylethylene diamine, N,N'-di-tert-butyl-1,4-tetramethylene diamine and N,N'-bis(1,1,3,3-tetramethylbutyl)-1,6-hexamethylene diamine.

In preferred amines where A represents a phenylene radical, $R^6$ is a secondary alkyl group, preferably a $C_{3-12}$ secondary alkyl group or a cyclohexyl group. Examples of such amines are N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine and N,N'-dicyclohexyl-p-phenylenediamine.

When any one of $R^1$, $R^4$ or $R^5$ is a $C_{3-6}$ alkyl group, this can be a straight- or branched-chain group. Preferred members of the $C_{1-6}$ alkyl series are methyl and ethyl; other examples are n-propyl, isobutyl, n-amyl, iso-amyl and n-hexyl.

Examples of the cyclic groups when $R^3$ and $R^5$ in formula (a)(ii) above are linked are those having the formulae

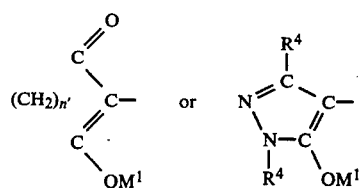

where n' has the value 2 or 3 and one or more of the hydrogen atoms in the $(CH_2)_{n'}$ grouping can be replaced by methyl or ethyl groups, and $R^4$ is as defined above. Specific examples of cyclic groups are 2-hydroxycyclopent-4-one-1-enyl, 2-hydroxy-cyclohex-5-one-1-enyl and 5-hydroxy-3-methyl-1-phenylpyrazol-4-yl.

Compounds of the formula (a) in which R represents $CCl_3$ can be prepared from the corresponding bis thiocyanates by reaction with chloroform in the presence of aqueous alkali metal hydroxide and a phase transfer catalyst, for example a tetra-alkylammonium hydroxide.

A general method for the synthesis of the stabiliser compounds of formula (a)(i) and (ii) comprises the reaction of a bis(thiolsulphonate) intermediate with a compound containing an active methylene group in a polar solvent in the presence of an alkali metal carboxylate, for instance sodium acetate. Preferred polar solvents are alkanols, for example methanol, ethanol or isopropanol. The reaction is conveniently carried out at the reflux temperature of the solvent at atmospheric pressure, for example at a temperature in the range 60°–100° C., but if desired, higher reaction temperature can be achieved by operating under pressure.

For the production of compounds having formula a(i) or a(ii) above, the compound containing an active methylene group is one having the formula

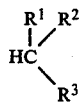

where $R^1$, $R^2$ and $R^3$ are as defined above. It will be appreciated that the group having the formula (ii) is the enol form of certain of the groups within formula (i). In the method described above, it is found that where $R^2$ or $R^3$ is a group containing a carbonyl group adjacent to the active methylene group and tautomerism is possible, then the enol form (formula ii) of the product is the one usually isolated from the reaction mixture.

Using the same bis(thiolsulphonate) intermediates and active methylene compounds, but in a reaction medium of an alkanol containing an alkali metal oxide, the principal product may be a compound of formula (a) but is more usually an oligomer of formula (b), with the other formed in smaller amounts. The reaction is normally carried out at a temperature within the range from 30° C. to the reflux temperature of the solution at atmospheric pressure, preferably within the range 40°–60° C.

Stabilisers where M or $M^1$ in the above formulae represents a metal or an ion derived from a nitrogenous base are suitably prepared via the corresponding compound in which M or $M^1$ is H. Conveniently, a solvent in which the required product is insoluble is selected as a medium in which to mix a source of the metal or base with the hydrogen form of the compound, the latter being soluble in the medium, so that the product precipitates and can be collected by filtration.

In another method for the preparation of compounds having formula a(i), the starting materials are dithiol HS—B—SH (preferably in the form of an alkali metal salt) and a compound having the formula

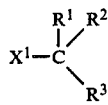

where $X^1$ is chlorine or bromine and $R^1$, $R^2$ and $R^3$ are as defined above. Polar solvent reaction media are suitable, for example $C_{1-3}$ alkanols or mixtures of these alcohols with water, and the reaction is usually carried out at a temperature above normal ambient temperature, and conveniently at the reflux temperature of the medium at atmospheric pressure.

Compounds which can be prepared by this method using the dithiol and chloroacetic acid include 1,6-bis(carboxymethylthio)hexane, 1,10-bis(carboxymethylthio)decane, [2'(carboxymethylthio)isopropyl]-(carboxymethylthio)-4-methylcyclohexane and [2'(carboxymethylthio)ethyl]-(carboxymethylthio)cyclohexane, and the corresponding zinc and nickel salts.

The stabiliser materials referred to above are especially effective in compositions in which the rubber is cis-polyisoprene, either natural or synthetic, and in blends containing at least 25% by weight of cis-polyisoprene with other rubbers. Preferably the rubber, if a blend, contains at least 40% and more preferably at least 60% by weight of cis-polyisoprene. Examples of other rubbers which may be blended with cis-polyisoprene include poly-1,3-butadiene, copolymers of 1,3-butadiene with other monomers, for example styrene, acrylonitrile, isobutylene and methyl methacrylate, and ethylene-propylene-diene terpolymers.

The amount of stabiliser compound employed in the compositions of the present invention is usually from 0.5 to 5, for example from 1.5 to 5, parts by weight, and preferably from 2 to 4 parts by weight per 100 parts by weight of rubber.

In the composition of the invention the essential vulcanising agent is sulphur, but other vulcanising agents such as amine disulphides need not be excluded. The amount of sulphur in the compositions is typically from 2 to 3 parts by weight per 100 parts by weight of rubber, but lesser or larger amounts, for example from 1 to 5 parts on the same basis, may be employed.

In the composition of the invention, a single accelerator or a mixture of accelerators can be employed. These include thiazole-based accelerators, for example 2-mercaptobenzothiazole, bis(2-benzothiazolyl)disulphide, benzothiazole-2-sulphenamides for instance N-isopropylbenzothiazole-2-sulphenamide, N-tert-butyl-benzothiazole-2-sulphenamide, N-cyclohexylbenzothiazole-2-sulphenamide, N,N-diisopropyl-benzothiazole-2-sulphenamide, N,N-dicyclohexyl-benzothiazole-2-sulphenamide and 2(morpholinothio)benzothiazole, thiocarbamylsulphenamides, for example N,N-dimethyl-N',N'-dicyclohexylthiocarbamylsulphenamide and N(morpholinothiocarbonylthio)morpholine. Mixtures of thiazole-based accelerators with diphenylguanidine can be used. Preferred accelerators are the benzothiazole-2-sulphenamides. In the compositions of the invention, these are usually used in amounts of from 0.5 to 1.5 part by weight per 100 parts by weight of rubber.

The vulcanisate stabilisers used in this invention can be incorporated into rubber by conventional mixing procedures, for example by adding them in a Banbury mixer or by adding them to the rubber on a mill. Ordinarily, with liquid or low melting solid vulcanisate stabilisers, no special precautions are necessary for obtaining good dispersions. However, when using higher melting vulcanisate stabilisers it is recommended that they be ground to a fine powder, preferably 70 micrometer particle size or less to ensure adequate dispersion. Such powders may be treated to suppress dust, for example by the addition of oil, or they can be mixed with a binder, for example a polymer latex, and formed into granules or pellets containing up to 5% by weight of binder. They can also be formulated as predispersions in certain rubbery polymers, such as EPDM or ethylene-vinyl acetate rubber, which predispersions may contain, for example, from 15 to 50% by weight of polymer.

The rubber stocks may include reinforcing carbon blacks, pigments such as titanium dioxide and silicon dioxide, metal oxide activators such as zinc oxide and magnesium oxide, stearic acid, hydrocarbon softeners and extender oils, amine, ether, and phenolic antioxidants, phenylenediamine antidegradants, and tackifiers. The stocks may also contain prevulcanization inhibitors but in many stocks their use is unnecessary.

Hexamethylene-1,6-dithiocyanate, useful as a vulcanisate stabiliser according to the present invention was prepared as follows:

1,6-Dibromohexane (36.6 g; 0.15 mole) and potassium thiocyanate (43.7 g; 0.45 mole) were refluxed for 3 hours in ethanol (300 ml). After cooling the reaction medium, the solid KBr was filtered off and the ethanol was evaporated in vacuo. The residual oil was dissolved in ether, washed with water several times, dried ($CaSO_4$) and the ether removed by evaporation, finally in vacuo to yield a colourless liquid (yield: 77%).

Decamethylene-1,10-dithiocyanate was prepared similarly from 1,10 dibromodecane and potassium thiocyanate.

The invention is illustrated by the following Examples.

EXAMPLE 1

This Example describes the preparation of hexamethylene-1,6-bis(acetylacetone sulphide). Hexane-1,6-bis(p-tolylthiosulphonate) (93.5 g; 0.204 mole) and acetylacetone (excess, 63 ml; 0.6 mole) were refluxed in 1,200 ml of EtOH for 1 hour in the presence of 55 g of sodium acetate. The mixture was cooled to $-5°$ C. and the solid separated by filtration nd washed with water.

Recrystallisation from isopropanol afforded needles (yield: 67%, melting point: 85°–86° C.).

I.R. Spectrum: 1,400–1,650 $cm^{-1}$: broad absorption

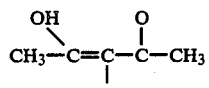

The NMR Spectrum is consistent with the enol structure:

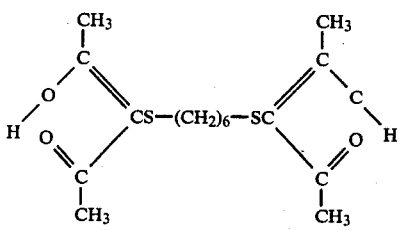

EXAMPLE 2

This Example describes the preparation of hexamethylene-1,6-bis(acetylacetone sulphide) sodium salt.

A solution of 27.68 gr of hexamethylene bis(acetylacetone sulphide) (0.08 mole) in 200 ml of $CH_2Cl_2$ was poured in 800 ml of isopropanol. To this mixture, an aqueous solution of sodium hydroxide (8 g of NaOH in 200 ml of $H_2O$) was added dropwise at 5°–10° C. (ice-water bath.) Then, the resulting mixture was stirred for 30 min at room temperature, the solid separated and dried under vacuo to yield a white powder (yield: 38 g).

I.R. Spectrum: 3,100–3,600 cm$^{-1}$ (broad absorption band with a maximum at 3,360 cm$^{-1}$): water of hydration 1,570 cm$^{-1}$ (shoulder at 1630 cm$^{-1}$): C—O absorption acetylacetonate group The structure was confirmed by an NMR analysis.

EXAMPLE 3

This Example describes the preparation of other metal salts of polymethylene-1,6-bis(acetylacetone sulphides).

An aqueous solution of NaOH (6 g. of NaOH in 100 ml. of $H_2O$) was added dropwise to a methanolic dispersion of hexamethylene bis(acetylacetone sulphide) (20.7 g., 0.06 mole in 600 ml. of $CH_3OH$) at 5°–10° C. (ice-water bath) with stirring, followed by the addition of an aqueous solution of a metal salt.

For the preparation of the nickel salt (3a), the solution contained 15.8 g. $NiSO_4\ 6H_2O$, for the preparation of the cupric salt (3b), the solution contained 10.2 g. of $CuCl_2.2H_2O$; and for the preparation of the zinc salt (3c), the solution contained 8.2 g. of $ZnCl_2$.

The mixture was stirred for 30 minutes at room temperature; the suspended solid at the end of that time was filtered off, resuspended in 1 liter of water, filtered, washed and dried under vacuum to give a power insoluble in most common solvents.

The nickel salt of decamethylene-1,10-bis(acetyl acetone sulphide) (3d) was prepared similarly from decamethylene bis(acetylacetone sulphide) (3e, prepared from decamethylene 1,10-bis(p-tolylthiosulphonate) and acetylacetone by a process similar to that of Example 1), NaOH and $NiSO_4\ 6H_2O$.

EXAMPLE 4

This Example describes the preparation of hexamethylene-1,6-bis(acetoacetanilide sulphide).

Sodium (5 g.) was dissolved in 250 ml. of absolute ethanol with stirring. Acetoacetanilide (36.15 g.) was added portionwise to the ethoxide solution. Then, hexane-1,6-bis(p-tolylthiosulphonate) (46,5 g) was added with 500 ml of absolute ethanol. The resulting mixture was stirred for 1 hour at 40°–50° C. After cooling, the ethanol was removed by distillation, chloroform was added and this organic phase was washed with water and dried. The removal of $CHCl_3$ afforded an oil which slowly solidified on standing.

I.R. Spectrum: 3,320 cm$^{-1}$ (N—H absorption) 1,680 cm$^{-1}$ (carbonyl group: amide function)

The NMR Spectra was consistent with the structure:

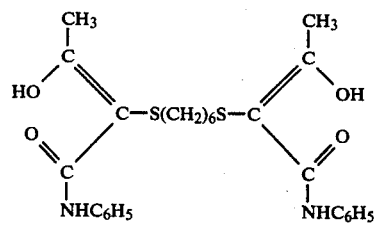

EXAMPLE 5

(a) Preparation of decamethylene-1,10-bis(dimedone sulphide). Decane-1,10-bis(p-tolylthiosulphonate) (10,5 g) and dimedone (3,3-dimethylcyclohexan-1,5-dione) (8,6 g) were refluxed in EtOH for 1 hr, in the presence of 5 g of sodium acetate. The mixture was cooled, and water was added, followed by $CH_2Cl_2$. The crude solid obtained was recrystallised from methanol—water (yield=90%).

The IR spectra showed the presence of broad absorption bands at 1500–1600 cm$^{-1}$, 3100–3500 cm$^{-1}$ assigned to the C=O group and OH (enol form). By NMR analysis, the structure of the compound is confirmed to be the wanted product.

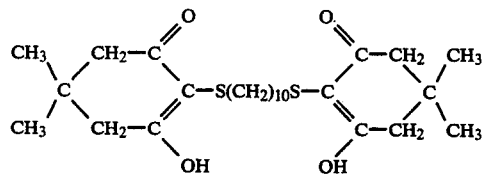

(b) Hexamethylene-1,6-bis(dimedone sulphide) was prepared similarly from hexane-1,6-bis(p-tolylthiosulphonate) and dimedone.

EXAMPLE 6

Preparation of hexamethylene-1,6-bis(3-methyl-1-phenylpyrazolone sulphide).

Sodium (5 g) was dissolved in 250 ml of absolute ethanol with stirring. 3-Methyl-1-phenylpyrazol-5-one (35,5 g) was added portionwise to the ethoxide solution. Then hexane-1,6-bis(p-tolylthiosulphonate) (46,5 g) was added with 500 ml of absolute ethanol. The resulting mixture was stirred for one hour at 40°–50° C. cooled and poured into 1.5 liters of water. The white solid was filtered off, washed with water and dried under vacuo (yield: 43,8 g, 87%; melting point: 169°–171° C.).

I.R. Spectrum: 2,000–3,200 broad absorption with a maximum at 2,600–2,700 cm$^{-1}$: OH absorption.

The NMR Spectrum was consistent with the enolic structure:

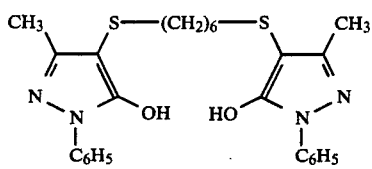

EXAMPLE 7

This Example describes the preparation of hexamethylene-1,6-bis[(diphenylsulphonyl)methane sulphide]

Sodium (1 g) was dissolved in 60 ml of absolute ethanol with stirring. Bis(phenylsulphonyl)methane (12.08 g) was added as a suspension in 200 ml of absolute ethanol to the ethoxide solution. The well-stirred mixture was heated to 50° C., then hexane 1,6-bis(p-tolylthiolsulphonate) (9.36 g) was added portionwise. The resulting mixture was stirred for 1 hour at 50° C., during which time the reaction mixture first became clear, followed by the appearance of a white solid. Water (500 ml) was added, the suspension was filtered, and the solid thus collected was washed with water. This product was stirred in hot methanol for 15 minutes, then isolated and dried. Yield 12 g, 80%.

I.R. Spectrum: 3,020 cm$^{-1}$: aromatic C—H 2,920; 2,840 cm$^{-1}$: aliphatic C—H 1,580; 1,180; 750; 660 cm$^{-1}$: aromatic ring 1,320; 1,150 cm$^{-1}$: —SO$_2$—group The NMR spectrum was consistent with the structure:

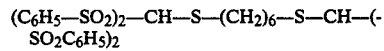

EXAMPLE 8

This Example describes the preparation of an oligomer by the reaction of sodium malonamide with decane-1,10-bis(p-tolylthiolsulphonate).

Sodium (1.9 g) was dissolved in 60 ml of absolute methanol with stirring in a flask fitted with a reflux condenser and a CaCl$_2$ tube. After dissolution of the sodium, malonamide (8.32 g) was added with 60 ml of absolute methanol and the resulting mixture heated at reflux and stirred for 10 min. Then, Decane-1,10-bis(p-tolylthiosulphonate) (21 g) was added in small portions with 150 ml absolute CH$_3$OH. This mixture was refluxed for 1 hour. The white solid obtained was filtered off, washed with water, CHCl$_3$ and dried under vacuum.

I.R. Spectrum: 3,050–3,500 cm$^{-1}$ (broad): —NH$_2$ 2,970 cm$^{-1}$; 2,930 cm$^{-1}$: —CH$_2$— 1,570–1,720 cm$^{-1}$ (broad): carbonyl (maximum at 1,660 cm$^{-1}$)

The NMR spectrum was consistent with the structure:

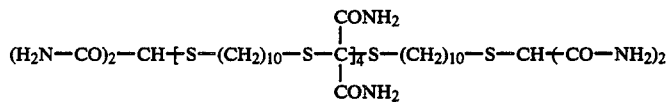

EXAMPLE 9

This Example describes the preparation of oligomers by the reaction of sodium cyanoacetamide with (a) decane-1,10-bis(p-tolylthiolsulphonate) and with (b) hexane-1,6-bis(p-tolylthiolsulphonate).

Sodium (1.05 g) was dissolved in 60 ml of absolute CH$_3$OH with stirring in a flask fitted with a reflux condenser and a CaCl$_2$ tube. Cyanoacetamide (3.5 g) was added to the methoxide solution with 60 ml of absolute CH$_3$OH and this mixture was stirred for 10 min. Decane-1,10 bis(p-tolylthiosulphonate), (10.5 g) or hexane-1,6-bis(p-tolylthiosulphonate), (9.2 g) was added in small portions with 100 ml of absolute CH$_3$OH. The resulting mixture was heated at 50° C. 1 hour with stirring. The reaction was quenched with water; the light coloured solid isolated was washed with water and dried under vacuum.

IR and NMR spectra were consistent with the structures:

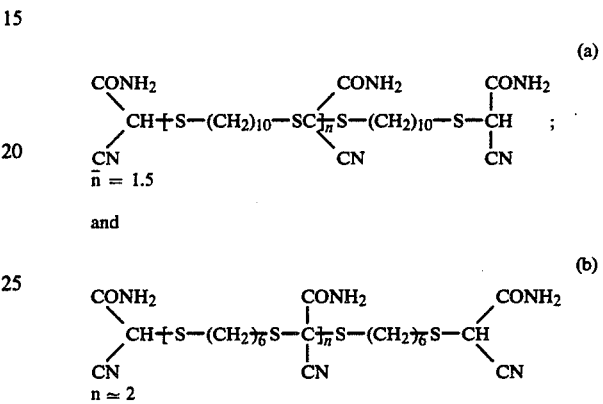

EXAMPLE 10

This Example describes the preparation of an oligomer by the reaction of sodium ethyl cyanoacetate with decane-1,1 bis(p-tolylthiolsulphonate).

The procedure was the same as that described in Example 9 up to the completion of the addition of the decane-1,10-bis(p-tolylthiolsulphonate), except that ethyl cyanoacetate (4.62 g) was used in place of cyanoacetamide. The stirred reaction mixture was heated at 50°–60° C. for 2 hours, and was then quenched with water, followed by the addition of methylene dichloride. The organic phase was separated, washed with water, dried, and the solvent was removed to give an oil.

IR and NMR spectra were consistent with the structure:

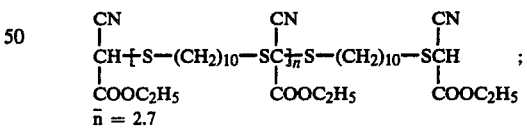

EXAMPLE 11

This Example describes the preparation of (a) hexane-1,6-bis(thioglycollic acid) and (b) zinc hexane-1,6-bis(-thioglycollate).

(a) An ethanolic solution of sodium hexane-1,6-dithiolate (made from 75 g. of hexane-1,6-dithiol in 300 ml.

of ethanol and 40 g. of sodium hydroxide dissolved in 200 ml. of water) was added to a solution of chloroacetic acid, sodium salt, in a mixture ethanol-water (made from 99.23 g. chloroacetic acid in 1300 ml. of ethanol and 42.5 g. of sodium hydroxide dissolved in 200 ml. of water). This mixture was refluxed for 6 hours with stirring. Ethanol-water azeotrope was removed by distillation, giving as residue an aqueous slurry which was poured into water (1500 ml.). Then an aqueous solution of HCl 2N was added until the pH of the dicarboxylate solution reached 2–2.5. The white solid formed was collected by filtration, washed with water and dried under vacuum (yield: 73%). Melting point: 116°–117° C.

The NMR spectrum was consistent with the proposed structure:

(b) Aqueous solution of zinc sulphate (43.2 g. of $ZnSO_4.7H_2O$ in 300 ml. of water) was added dropwise to a solution of hexane-1,6-bis(thioglycollic acid) sodium salt (made from 40 g. of hexane-1,6-bis(-thioglycollic acid) in 1000 ml. of methanol and 12.02 g. of sodium hydroxide dissolved in 200 ml. of water). A white solid precipitated, and the mixture was stirred at room temperature for 30 min. The solid was collected by filtration, resuspended in water (1000 ml.) and the suspension was stirred for 15 min. Then it was filtered and the solid was washed with water and dried under vacuum. (Yield: 47 g.).

EXAMPLE 12

This example describes the preparation of hexane-1,6-bis(trichloromethyl sulphide).

Hexane-1,6-bis thiocyanate (20 g.), chloroform (76 g.) and tetrabutylammonium hydroxide (1.5 g. of 40% solution) were stirred vigorously in a flask. 50% aqueous sodium hydroxide solution (40 ml.) was added portionwise and the resulting mixture was stirred for 3–4 hours at 40° C. The mixture was then cooled, poured into water and extracted with chloroform. The chloroform solution was washed several times with water, dried over calcium sulphate, and the solvent was evaporated. The residue was a dark red liquid. Yield: 25.5 g. (65%). The NMR spectrum confirmed the structure $Cl_3C—S—(CH_2)_6—S—CCl_3$.

EXAMPLE 13

This example describes the preparation of amine salts of hexane-1,6-bis(thioglycollic acid).

(a) A solution of N-benzyl-N-1,1,3,3-tetramethylbutylamine (26.8 g.) in methanol (100 ml.) was added dropwise to a solution of the acid (16 g.) in methanol (600 ml.) at room temperature. The mixture was stirred for 30 minutes, and the solvent was then removed, giving the amine salt as a residue (42 g.).

(b) The N-isopropyl-N'-phenyl-p-phenylenediamine salt of hexane-1,6-bis(thioglycollic acid) was prepared similarly.

EXAMPLE 14

A bis(thioglycollic acid) (a) and its zinc salt (b) were prepared by processes similar to those described in Example 11 from dipentene dimercaptan,

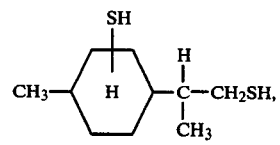

sodium chloroacetate and zinc sulphate.

EXAMPLE 15

A bis(thioglycollic acid) derivative was prepared from ethylcyclohexyl dimercaptan

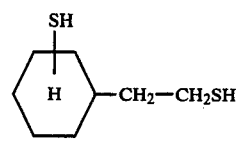

and sodium chloroacetate by a process similar to that described in Example 11.

EXAMPLE 16

To evaluate the use of the vulcanisate stabilisers according to this invention in natural rubber vulcanisates, a masterbatch having the following composition was prepared:

|  | Parts by Weight |
| --- | --- |
| Natural rubber | 100 |
| Carbon Black | 50 |
| Zinc Oxide | 5 |
| Stearic Acid | 2 |
| Processing Oil | 3 |
| N—phenyl-N'—(1,3-dimethylbutyl)-p-phenylenediamine (Antidegradant) | 2 |

Portions of the masterbatch were taken and mixed with sulphur, 2(morpholinothio)benzothiazole and the stabiliser compound in the proportions 2.5, 0.7 and 3.0 parts by weight respectively per 100 parts by weight of rubber. A further portion of masterbatch to which only sulphur and 2(morpholinothio)benzothiazole were added was used as a control.

The curing characteristics of the vulcanisable compositions thus obtained were determined at the curing temperatures shown in the Table below by means of the Monsanto Oscillating Disc Rheometer ISO 3417-1977(E) with a 1° amplitude of oscillation. From the Rheometer data, the time (t. max.) required to reach maximum torque (maximum modulus) was recorded. Vulcanisates were prepared by press curing at 141° C. for the time (t. max.) indicated by the Rheometer data to give maximum modulus. Other vulcanisates were prepared at the same temperature but were held at this temperature for 200 minutes (overcure). Both types of vulcanisate were subjected to conventional methods of physical testing. Resilience measurements were carried out according to British Standard 903 Part A8 (1963).

In the Table below, the stabiliser compounds are identified as "A" for hexamethylene-1,6-dithiocyanate, "B" for decamethylene-1,10-dithiocyanate, and by numbers according to the preceding Examples. Figures shown in parenthesis are those obtained for the corresponding controls.

| Compound | 300% Modulus (MPa)[1] | % Retention of 300% Modulus on overcure[2] |
| --- | --- | --- |
| A | 16.1 (17.7) | 106 (80) |
| B | 15.8 (17.7) | 89 (80) |
| 1 | 14.2 (16.0) | 114 (89) |
| 2 | 16.2 (17.0) | 99 (88) |
| 3a | 17.5 (17.2) | 94 (84) |
| 3b | 14.7 (14.5) | 96 (91) |
| 3c | 14.2 (14.5) | 104 (91) |
| 3d | 14.9 (16.5) | 109 (81) |
| 3e | 15.6 (15.8) | 108 (94) |
| 4 | 15.1 (14.5) | 99 (91) |
| 5(a) | 19.9 (18.1) | 91 (81) |
| 5(b) | 15.5 (16.0) | 101 (89) |
| 6 | 14.9 (14.5) | 103 (91) |
| 8 | 14.7 (15.5) | 102 (84) |
| 9(a) | 15.5 (16.5) | 103 (81) |
| 9(b) | 15.1 (16.9) | 107 (82) |
| 10 | 14.4 (16.5) | 104 (81) |
| 11(b) | 16.5 (16.0) | 102 (87) |
| 12[3] | 16.3 (16.0) | 108 (84) |
| 13(a) | 16.3 (14.6) | 96 (90) |
| 13(b) | 15.0 (15.3) | 95 (89) |
| 14(a) | 15.0 (14.6) | 99 (90) |
| 14(b) | 15.0 (14.6) | 101 (90) |
| 15 | 16.3 (17.4) | 95 (85) |

[1]Sample cured to t max
[2]Results for sample cured for 200 minutes expressed as a percentage of the result for sample cured to t max.
[3]Composition contained 1.5 parts phr of stabiliser.

(1) Sample cured to t max
(2) Results for sample cured for 200 minutes expressed as a percentage of the result for sample cured to t max.
(3) Composition contained 1.5 parts phr of stabiliser.

These results show the value of the stabiliser compounds in alleviating the adverse effects of overcure.

We claim:

1. A vulcanizable rubber composition comprising a diene rubber, sulphur and a vulcanisation accelerator, characterised in that the composition also comprises a stabiliser material having the formula (a) R—S—B—S—R where B is an organic bridging group selected from the group consisting of an alkylene or alkenylene radical having 2 to 40 carbon atoms which is optionally substituted by one or more aryl substituents, a cycloalkylene, a ($C_{1-6}$ alkylene) cycloalkylene, a ($C_{1-6}$ alkylene) alkylcycloalkane or one of the structures having the following formulae:

—$(CH_2)_a$—O—$(CH_2)_a$—
—$(CH_2)_a$—O—$(CH_2)_{a'}$—O—$(CH_2)_a$—
—$(CH_2)_b$—A—$(CH_2)_b$—
—$(CH_2)_c$—COO—$(CH_2)_a$— and
—$(CH_2)_c$—COO—Y—OOC—$(CH_2)_c$—, where each a' and each c independently represents an integer of from 1 to 20, a represents an integer of from 2 to 20, each b independently represents an integer of from 1 to 10, A represents phenylene or cyclohexylene, and Y represents a group —$(CH_2)_c$— or a group —$(CH_2CH_2O)_dCH_2CH_2$— where d represents an integer of from 1 to 5 and R is (i) a group having the formula

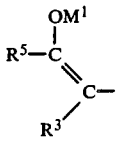

in which $M^1$ represents H, a monovalent metal or the equivalent of a multivalent metal, and wherein $R^3$ is CN, $CONHR^4$, $COR^5$, $COOR^5$, $SO_2R^5$, COOM or $SO_2OM$, where $R^4$ is H, $C_{1-6}$ alkyl, phenyl or benzyl, and $R^5$ is $C_{1-6}$ alkyl, phenyl or benzyl, or in which $R^3$ and $R^5$ are linked to form a cyclic group having the formula

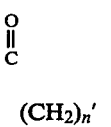

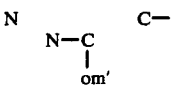

where n' has the value 2 or 3 and one or more of the hydrogen atoms in the $(CH_2)_{n'}$ grouping can be replaced by methyl or ethyl groups, and B in the formula of the stabilizer represents an alkylene group having from 5 to 6 carbon atoms j or (ii) CN or $CCl_3$; or

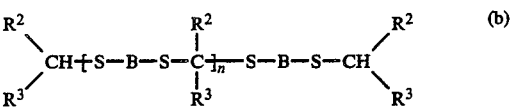

where n has an average value of from 1 to 5.

2. A composition according to claim 1 wherein the stabiliser is a compound having formula (a) (i) wherein B represents an alkylene group having from 5 to 16 carbon atoms, $R^3$ represents $COR^5$, each $R^5$ independently represents methyl or ethyl, and $M^1$ represents H, an alkali metal, or an equivalent of copper, zinc, or nickel.

3. A composition according to claim 2 wherein the stabiliser is the zinc salt of hexamethylene-1,6-bis(acetylacetone sulphide).

4. A composition according to claim 1 wherein the stabiliser is a compound having formula (a) (i) wherein B represents an alkylene group having from 5 to 16 carbon atoms, $R^3$ is $R^4NHCO$ and $R^5$ is methyl or ethyl.

5. A composition according to claim 1 wherein R in the formula of the stabiliser represents a cyclic group having the formula

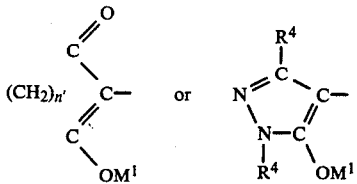

where n' has the value 2 or 3 and one or more of the hydrogen atoms in the $(CH_2)_{n'}$ grouping can be replaced by methyl or ethyl groups, and B in the formula of the stabiliser represents an alkylene group having from 5 to 16 carbon atoms.

6. A composition according to claim 5 wherein the stabiliser is hexamethylene-1,6-bis(3-methyl-1-phenyl-pyrazolone sulphide).

7. A composition according to claim 1 wherein the stabiliser is a compound having formula (a) (ii) in which B represents an alkylene group having from 5 to 6 carbon atoms.

8. A composition according to claim 1 wherein the stabiliser is a material of formula (b) wherein $R^2$ and $R^3$ are each independently CN, $CONHR^4$ or $COOR^5$, and B represents an alkylene group having from 5 to 16 carbon atoms.

9. A composition according to claim 8 where $R^4$ is H and $R^5$ is methyl or ethyl.

10. A composition according to claim 9 wherein the stabiliser has the formula

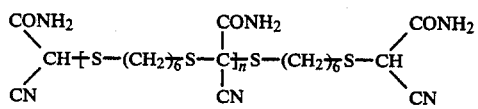

where n has an average value of from 1 to 3.

11. A composition according to claim 1 in which the amount of the stabiliser material is from 1.5 to 5 parts by weight per 100 parts by weight of rubber.

12. A composition according to claim 1 in which the diene rubber is cis-polyisoprene or a blend of diene rubbers containing at least 40% by weight of cis-polyisoprene.

13. A vulcanisate that has been obtained by heating a composition according to claim 1 at a vulcanisation temperature.

14. A compound having the formula
R—S—B—S—R
where B is an alkylene group having from 5 to 16 carbon atoms and R is a group having the formula

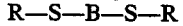

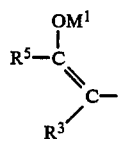

in which $M^1$ represents H, a monovalent metal or the equivalent of a multivalent metal, $R^3$ represents $CONHR^4$ or $COR^5$ where $R^4$ is H, $C_{1-6}$ alkyl, phenyl or benzyl, and $R^5$ is $C_{1-6}$ alkyl, phenyl or benzyl.

15. A compound according to claim 14, wherein B represents an alkylene group having from 5 to 16 carbon atoms, $R^3$ represents $COR^5$, each $R^5$ independently represents methyl or ethyl, and $M^1$ represents H, an alkali metal, or an equivalent of copper, zinc, or nickel.

16. The zinc salt of hexamethylene-1,6-bis(acetylacetone sulphide).

17. A compound according to claim 14 wherein $M^1$ represents H, sodium or an equivalent of zinc, $R^3$ is $C_6H_5NHCO$ and $R^5$ is methyl or ethyl.

18. A compound having the formula
R—S—B—S—R
where B is an alkylene group having from 5 to 16 carbon atoms and each R is a group having the formula

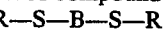

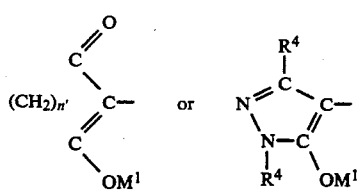

where n' has the value 2 or 3 and one or more of the hydrogen atoms in the $(CH_2)_{n'}$ grouping can be replaced by methyl or ethyl groups, $M^1$ represents H, a monovalent metal or the equivalent of a multivalent metal, and each $R^4$ independently represents methyl, ethyl or phenyl.

19. The compounds hexamethylene-1,6-bis(dimedone sulphide), decamethylene-1,10-bis(dimedone sulphide) and hexamethylene-1,6-bis(3-methyl-1-phenylpyrazolone sulphide).

20. A material having the formula

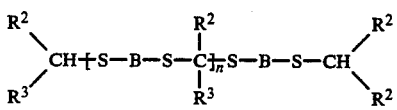

where B represents an alkylene group of from 5 to 16 carbon atoms, $R^2$ and $R^3$ are each independently CN, $CONHR^4$ or $COOR^5$ where $R^4$ is H, $C_{1-6}$ alkyl, phenyl or benzyl, $R^5$ is $C_{1-6}$ alkyl, phenyl or benzyl, and n has an average value of from 1 to 5.

21. A material according to claim 20 in which (i) both $R^2$ and $R^3$ are $CONH_2$ (ii) $R^2$ is CN and $R^3$ is $CONH_2$, or (iii) $R^2$ is CN and $R^3$ is $COOC_2H_5$.

22. A material having the formula

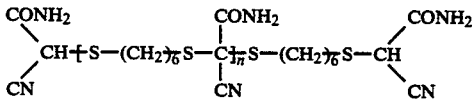

where n has an average value of from 1 to 3.

* * * * *